(12) United States Patent
Haraden et al.

(10) Patent No.: US 10,514,753 B2
(45) Date of Patent: Dec. 24, 2019

(54) SELECTIVELY APPLYING REPROJECTION PROCESSING TO MULTI-LAYER SCENES FOR OPTIMIZING LATE STAGE REPROJECTION POWER

(71) Applicant: MICROSOFT TECHNOLOGY LICENSING, LLC, Redmond, WA (US)

(72) Inventors: Ryan Scott Haraden, Duvall, WA (US); Jeffrey Powers Bradford, Woodinville, WA (US); Miguel Comparan, Kenmore, WA (US); Adam James Muff, Woodinville, WA (US); Gene Leung, Sammamish, WA (US); Tolga Ozguner, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 15/470,790

(22) Filed: Mar. 27, 2017

(65) Prior Publication Data
US 2018/0275748 A1    Sep. 27, 2018

(51) Int. Cl.
*G06F 3/01* (2006.01)
*G02B 27/01* (2006.01)
*H04N 5/74* (2006.01)

(52) U.S. Cl.
CPC ......... *G06F 3/012* (2013.01); *G02B 27/017* (2013.01); *H04N 5/7491* (2013.01); *A61M 2205/507* (2013.01); *A63F 2300/8082* (2013.01); *G02B 2027/0187* (2013.01)

(58) Field of Classification Search
None
See application file for complete search history.

(56) References Cited

U.S. PATENT DOCUMENTS

| 5,864,342 A * | 1/1999 | Kajiya ............... G06T 11/001 |
| | | 345/418 |
| 5,933,125 A | 8/1999 | Fernie et al. |
| 6,008,820 A | 12/1999 | Chauvin et al. |
| 6,057,847 A | 5/2000 | Jenkins |

(Continued)

FOREIGN PATENT DOCUMENTS

| CA | 2857832 | 1/2015 |
| EP | 2642398 A1 | 9/2013 |

(Continued)

OTHER PUBLICATIONS

U.S. Appl. No. 15/470,737, filed Mar. 27, 2017, Haraden et al.
(Continued)

*Primary Examiner* — Motilewa Good Johnson
(74) *Attorney, Agent, or Firm* — Workman Nydegger

(57) ABSTRACT

Optimizations are provided for late stage reprojection processing for a multi-layered scene. A multi-layered scene is generated. Late stage reprojection processing is applied to a first layer and different late stage reprojection processing is applied to a second layer. The late stage reprojection processing that is applied to the second layer includes one or more transformations that are applied to the second layer. After the late stage reprojection processing on the various layers is complete, a unified layer is created by compositing the layers together. Then, the render the unified layer is rendered.

25 Claims, 11 Drawing Sheets

(56) References Cited

U.S. PATENT DOCUMENTS

| | | | |
|---|---|---|---|
| 6,111,582 A | 8/2000 | Jenkins | |
| 6,449,395 B1 | 9/2002 | Kobayashi | |
| 6,456,340 B1* | 9/2002 | Margulis | G06T 1/20 |
| | | | 345/501 |
| 7,071,935 B1 | 7/2006 | Deering et al. | |
| 7,324,695 B2 | 1/2008 | Krishnan et al. | |
| 7,369,134 B2 | 5/2008 | Collins et al. | |
| 8,797,356 B2 | 8/2014 | Leung | |
| 9,117,309 B1 | 8/2015 | Crow | |
| 9,443,355 B2 | 9/2016 | Chan et al. | |
| 9,554,132 B2 | 1/2017 | Crewnshaw et al. | |
| 9,602,766 B2 | 3/2017 | Hines et al. | |
| 9,747,726 B2* | 8/2017 | Williams | G06T 19/006 |
| 9,817,547 B2 | 11/2017 | Varela et al. | |
| 9,819,970 B2 | 11/2017 | Sermadevi et al. | |
| 2004/0095357 A1* | 5/2004 | Oh | G06T 15/205 |
| | | | 345/589 |
| 2005/0132385 A1* | 6/2005 | Bourges-Sevenier | |
| | | | H04N 21/23412 |
| | | | 719/328 |
| 2007/0040851 A1 | 2/2007 | Brunner et al. | |
| 2008/0034292 A1* | 2/2008 | Brunner | G06T 13/00 |
| | | | 715/700 |
| 2008/0158254 A1 | 7/2008 | Jiang | |
| 2008/0165181 A1 | 7/2008 | Wang et al. | |
| 2008/0297437 A1* | 12/2008 | Takahashi | G02B 27/017 |
| | | | 345/8 |
| 2009/0002379 A1 | 1/2009 | Baeza et al. | |
| 2009/0016333 A1 | 1/2009 | Wang et al. | |
| 2009/0160857 A1 | 6/2009 | Rasmusson et al. | |
| 2009/0167785 A1 | 7/2009 | Wong | |
| 2010/0026712 A1* | 2/2010 | Aliprandi | H04N 13/111 |
| | | | 345/629 |
| 2011/0115792 A1 | 5/2011 | Tamaoki | |
| 2011/0267482 A1* | 11/2011 | Wetzstein | G06T 5/50 |
| | | | 348/218.1 |
| 2012/0139918 A1* | 6/2012 | Michail | G06T 15/503 |
| | | | 345/421 |
| 2012/0218381 A1* | 8/2012 | Uro | H04N 21/426 |
| | | | 348/43 |
| 2013/0222385 A1* | 8/2013 | Dorsey | G06T 11/20 |
| | | | 345/427 |
| 2013/0266292 A1* | 10/2013 | Sandrew | H04N 9/79 |
| | | | 386/282 |
| 2014/0071116 A1 | 3/2014 | Johansson et al. | |
| 2014/0177959 A1 | 6/2014 | Bar-On | |
| 2015/0002542 A1* | 1/2015 | Chan | G06F 3/048 |
| | | | 345/633 |
| 2015/0022522 A1* | 1/2015 | Li | G06T 19/00 |
| | | | 345/424 |
| 2015/0029218 A1* | 1/2015 | Williams | G06T 19/006 |
| | | | 345/633 |
| 2015/0213640 A1* | 7/2015 | Neill | G06T 7/0075 |
| | | | 345/427 |
| 2015/0235430 A1 | 8/2015 | Schowengerdt et al. | |
| 2015/0304665 A1* | 10/2015 | Hannuksela | H04N 19/70 |
| | | | 375/240.02 |
| 2015/0310665 A1 | 10/2015 | Michail et al. | |
| 2015/0339234 A1 | 11/2015 | Karandikar et al. | |
| 2015/0378920 A1 | 12/2015 | Gierach et al. | |
| 2015/0379772 A1 | 12/2015 | Hoffman | |
| 2016/0035139 A1 | 2/2016 | Fuchs et al. | |
| 2016/0093098 A1* | 3/2016 | Andersson | G06T 11/40 |
| | | | 345/426 |
| 2016/0110919 A1 | 4/2016 | Hancock et al. | |
| 2016/0125658 A1 | 5/2016 | Sugden | |
| 2016/0136816 A1 | 5/2016 | Pistorino | |
| 2016/0148067 A1 | 5/2016 | Bottou et al. | |
| 2016/0189429 A1 | 6/2016 | Mallinson | |
| 2016/0219325 A1* | 7/2016 | Chu | H04N 21/42653 |
| 2016/0299567 A1* | 10/2016 | Crisler | G06F 3/011 |
| 2016/0321774 A1 | 11/2016 | Liang et al. | |
| 2016/0335795 A1* | 11/2016 | Flynn | G06T 15/20 |
| 2016/0343164 A1 | 11/2016 | Urbach et al. | |
| 2017/0003764 A1* | 1/2017 | Li | G06T 19/006 |
| 2017/0039765 A1 | 2/2017 | Zhou et al. | |
| 2017/0148222 A1* | 5/2017 | Holzer | H04N 13/243 |
| 2017/0200308 A1* | 7/2017 | Nguyen | G06T 3/0012 |
| 2017/0213388 A1 | 7/2017 | Margolis et al. | |
| 2017/0221176 A1 | 8/2017 | Munteanu et al. | |
| 2017/0262045 A1* | 9/2017 | Rouvinez | G06F 3/011 |
| 2017/0308988 A1* | 10/2017 | Li | G06T 11/40 |
| 2017/0372457 A1* | 12/2017 | Sylvan | G02B 27/017 |
| 2018/0005443 A1 | 1/2018 | Poulos et al. | |
| 2018/0260931 A1 | 9/2018 | Ozguner et al. | |
| 2018/0276824 A1 | 9/2018 | Haraden et al. | |
| 2018/0301125 A1 | 10/2018 | Haraden et al. | |
| 2019/0189089 A1 | 6/2019 | Haraden et al. | |

FOREIGN PATENT DOCUMENTS

| | | |
|---|---|---|
| EP | 3051525 | 8/2016 |
| WO | 2006087665 A2 | 8/2006 |

OTHER PUBLICATIONS

U.S. Appl. No. 15/415,569, filed Jan. 25, 2017, Ozguner et al.

U.S. Appl. No. 15/415,542, filed Jan. 25, 2017, Ozguner et al.

Abrash, Michael, "Latency—the sine qua non of AR and VR", http://blogs.valvesoftware.com/abrash/latency-the-sine-qua-non-of-ar-and-vr/, Published on: Dec. 29, 2012, 153 pages.

Abrash, Michael, "Latency—the sine qua non of AR and VR", http://blogs.valvesoftware.com/abrash/latency-the-sine-qua-non-of-ar-and-vr/, Published on: Dec. 29, 2012, 73 pages.

Boos, et al., "Flash Back: Immersive Virtual Reality on Mobile Devices via Rendering Memoization", In Proceedings of the 14th Annual International Conference on Mobile Systems, Applications, and Services, Jun. 25, 2016, 13 pages.

Chikhale, et al., "Hybrid Multi-level Cache Management Policy", In Proceedings of Fourth International Conference on Communication Systems and Network Technologies, Apr. 7, 2014, pp. 1119-1123.

Friston, et al., "Construction and Evaluation of an Ultra Low Latency Frameless Renderer for VR", Apr. 2016, pp. 1377-1386.

Jeffries, Freddi, "Virtual Reality—Blatant Latency and how to Avoid it", https://community.arm.com/groups/arm-mali-graphics/blog/2016/03/01/virtual-reality-blatant-latency-and-how-to-avoid-it, Published on: Mar. 1, 2016, 9 pages.

Kalarat, Kosin, "Applying Relief Mapping on Augmented Reality", In Proceedings of 12th International Joint Conference on Computer Science and Software Engineering, Jul. 22, 2015, 3 pages.

Kang, et al., "Multi-layered Image-Based Rendering", In Proceedings of the Graphics Interface Conference, Jun. 2, 1999, 9 pages.

Orland, Kyle, "How fast does "virtual reality" have to be to look like "actual reality"?", http://arstechnica.com/gaming/2013/01/how-fast-does-virtual-reality-have-to-be-to-look-like-actual-reality/, Published on: Jan. 4, 2013, 3 pages.

Notice of Allowance issued in U.S. Appl. No. 15/415,542 dated Jan. 22, 2018.

"Non Final Office Action Issued in U.S. Appl. No. 15/415,569", dated Jun. 28, 2018, 19 Pages.

"Non Final Office Action Issued in U.S. Appl. No. 15/979,983", dated Jul. 17, 2018, 22 Pages.

Alameldeen, et al., "Interactions Between Compression and Prefetching in Chip Multiprocessors", In Proceedings of IEEE 13th International Symposium on High Performance Computer Architecture, Feb. 10, 2007, pp. 228-239.

Bright, Peter, "Microsoft Sheds Some Light on its Mysterious Holographic Processing Unit", Retrieved From: https://arstechnica.com/information-technology/2016/08/microsoft-sheds-some-light-on-its-mysterious-holographic-processing-unit/, Aug. 24, 2016, 6 Pages.

"International Search Report and Written Opinion Issued in PCT Application No. PCT/US2018/013038", dated Mar. 28, 2018, 14 Pages.

"International Search Report and Written Opinion Issued in PCT Application No. PCT/US2018/013039", dated Mar. 28, 2018, 13 Pages.

(56) References Cited

OTHER PUBLICATIONS

"International Search Report and Written Opinion Issued in PCT Application No. PCT/US2018/023212", dated Jun. 12, 2018, 11 Pages.

"International Search Report and Written Opinion Issued in PCT Application No. PCT/US2018/023213", dated Jun. 6, 2018, 13 Pages.

"International Search Report and Written Opinion Issued in PCT Application No. PCT/US2018/025777", dated Jul. 25, 2018, 12 Pages.

Tseng, Juin-Ling, "Development of a Low-Cost 3D Interactive VR System using SBS 3D Display, VR Headset and Finger Posture Motion Tracking", In International Journal of Advanced Studies in Computers, Science and Engineering, vol. 5, Issue 8, Aug. 31, 2016, pp. 6-12.

"Final Office Action Issued in U.S. Appl. No. 15/470,737", dated Apr. 1, 2019, 9 Pages.

"Timewarp", Retrieved From: https://web.archive.org/web/20181222060247/https://xinreality.com/mediawiki/index.php?title=Timewarp&oldid=18615, Nov. 29, 2016, 3 Pages.

"Non Final Office Action Issued in U.S. Appl. No. 15/470,737", dated Nov. 8, 2018, 19 Pages.

Hamilton, Ian, "Valve's Answer to Asynchronous Timewarp Arrives (Update)", Retrieved From: https://uploadvr.com/valve-oculus-atw-reprojection/, Oct. 25, 2016, 6 Pages.

\* cited by examiner

1300

- 1310 — Generate A Scene That Includes One Or More Layers, The Scene Being Generated Based On A First Predicted Pose Of A Portion Of The Computer System.

- 1320 — Identify A Sub-region Within The One Or More Layers, The Sub-region Being Distinguished From At Least One Other Region In The One Or More Layers.

- 1330 — Isolate The Sub-region From The At Least One Other Region Of The One Or More Layers.

- 1340 — Apply Late Stage Reprojection Processing To The Isolated Sub-region While Refraining From Applying Late Stage Reprojection Processing To The At Least One Other Region Of The One Or More Layers.

*Figure 13*

SELECTIVELY APPLYING REPROJECTION PROCESSING TO MULTI-LAYER SCENES FOR OPTIMIZING LATE STAGE REPROJECTION POWER

CROSS-REFERENCE TO RELATED APPLICATIONS

Not Applicable

BACKGROUND OF THE INVENTION

Computers and computing systems have impacted nearly every aspect of modern living. Computers are generally involved in work, recreation, healthcare, transportation, entertainment, household management, etc.

Mixed-reality computer systems, which include virtual-reality systems and augmented-reality systems, have recently received significant interest for their ability to create immersive experiences for users. Conventional augmented-reality systems create an augmented-reality scenario by visually presenting virtual objects in the real world. In contrast, conventional virtual-reality systems create a more immersive experience such that a user's entire view is obstructed by a virtual world. As used herein, mixed-reality, augmented-reality, and virtual-reality systems are described and referenced interchangeably. Unless specifically stated or unless specifically required, as understood by one of skill in the art, the descriptions herein apply equally to any type of mixed-reality system, including augmented-reality systems, virtual-reality systems, and/or any other similar system capable of displaying virtual objects to a user.

Mixed-reality computer systems typically use one or more on-body devices (e.g., a head-mounted device, a handheld device, etc.). The head-mounted device provides a display, sometimes referred to as a head-mounted display (hereinafter "HMD"), that enables a user to view overlapping and/or integrated visual information in the user's ambient environment. For example, a mixed-reality system may present visual information to the user, through the HMD, in the form of a simulated object on an actual table surface.

Continued advances in hardware capabilities and rendering technologies have greatly increased the realism of virtual objects and scenes displayed to a user within a mixed-reality environment. For example, in mixed-reality environments, virtual objects can be placed within the real world in such a way as to give the impression that the virtual object is part of the real world. As a user moves around within the real world, the mixed-reality environment automatically updates so that the user is provided with the proper perspective and view of the virtual object. This mixed-reality environment is often referred to as a computer-generated scene, or simply a "scene."

In such systems, the user's body (specifically the user's head and corresponding HMD) can move in real-time in relation to the virtual environment. For example, in a mixed-reality application, if the user tilts her head in one direction, she would not expect the image or hologram to tilt with them. Ideally, the system would measure the position of the user's head and render images at a fast enough rate to eliminate any jitter or drift in the image position, as perceived by the user. However, typical graphics processing units ("GPU") currently render frames between only 30 to 60 frames per second, depending on the quality and performance of the GPU. This results in a potential delay of 16 to 33 milliseconds between the point in time of when the head position is detected and when the image is actually displayed on the HMD. Additional latency can also be associated with the time that is required to determine the new head position and/or delays between the GPU's frame buffer and the final adjusted display. The result is a potentially large error between where the user would expect an image and where the image is actually displayed, thereby degrading the user experience. In some instances, the user can also experience discomfort and disorientation when the virtual images are not presented in the appropriate locations, particularly during movement of the user's head and HMD.

In an effort to reduce or eliminate some of the foregoing rendering errors, existing systems apply late stage corrections to make final adjustments to the image after the image rendered by the GPU. This process is performed before the pixels are displayed so as to compensate for the latest rotation, translation, and/or magnifications resulting from the user's head movement. This adjustment process is often referred to as "Late State Adjustment", "Late Stage Reprojection", "LSR" or "LSR Adjustments." Hereinafter, this disclosure will use the abbreviation "LSR." Since frames can be rendered at a high rate and with high resolution, existing systems that employ LSR can require a large amount of DRAM bandwidth and power. It will be appreciated that, in the context of a wireless and battery-powered HMD, chip size as well as bandwidth and power requirements can be very important, which can add to the challenges and difficulties associated with rendering mixed-reality scenes to a user.

As suggested above, many mixed-reality computer systems are untethered battery-powered devices that suffer operational power constraints. These constraints are designed to prolong the battery's lifespan so that the user can enjoy more time with the scene. However, many operations of the computer system significantly impact the computer system's battery lifespan. For example, performing data acquisition operations and LSR actions are prime examples of such battery-tolling operations. Accordingly, there exists a strong need in the field to efficiently improve the power consumption of systems that perform these types of operations.

The subject matter claimed herein is not limited to embodiments that solve any disadvantages or that operate only in environments such as those described above. Rather, this background is provided to illustrate only one exemplary technology area where some embodiments described herein may be practiced.

BRIEF SUMMARY OF THE INVENTION

Embodiments disclosed herein relate to systems, hardware storage devices, and methods that optimize LSR processing.

Some embodiments generate a computer-generated scene that includes a plurality of layers. Further, the embodiments cause LSR processing to be applied to at least one of the layers (e.g., to a first layer in the plurality of layers). The embodiments also cause LSR processing to be applied to another layer (e.g., a second layer in the plurality of layers). The LSR processing of the second layer is performed independently from the LSR processing that is applied to the first layer. Further, the LSR processing that is applied to the second layer also includes one or more transformations. These transformations are applied to the second layer, but, in some instances, they are not applied to the first layer. The embodiments also create a unified layer. This unified layer is formed by compositing the transformed second layer with the first layer. Thereafter, the embodiments cause the unified layer to be rendered.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 13 illustrates an exemplary method for optimizing LSR processing.

DETAILED DESCRIPTION OF THE INVENTION

By way of introduction, the embodiments disclosed herein relate to systems, hardware storages devices, and methods that optimize LSR processing. To that end, the disclosed embodiments generate a computer-generated scene that includes a plurality of layers. The disclosed embodiments also cause LSR processing to be applied to at least one of the layers (e.g., to a first layer in the plurality of layers). The LSR processing is also applied to another layer (e.g., a second layer in the plurality of layers). The LSR processing of the second layer is performed independently from the LSR processing that is applied to the first layer. The LSR processing that is applied to the second layer includes one or more transformations that are applied to the second layer, but, in some instances, that are not applied to the first layer. The embodiments also create a unified layer. This unified layer is formed by compositing the transformed second layer with the first layer. Thereafter, the unified layer is rendered on the user device.

As will be discussed later, the embodiments described herein overcome many deficiencies prevalent throughout the conventional technology. Further, these embodiments provide for many other substantial benefits that will also be described throughout the remainder of this disclosure.

The following passage is provided as an initial guide to the subject matter of this disclosure. In particular, this disclosure will initially use FIG. 1 to present some introductory discussion of a computing system. Following that discussion, some introductory subject matter on LSR processing is provided. Then, this disclosure expounds on FIG. 2, which presents subject matter on a computer system capable of optimizing LSR processing performed on a multi-layered scene. FIGS. 3-12 will then be discussed. These figures provide detail on the use of multiple layers in a computer-generated scene where LSR is performed. Lastly, additional supporting architectures and methods using the novel principles described herein will be detailed with respect to the subsequent figures.

Figure 1:
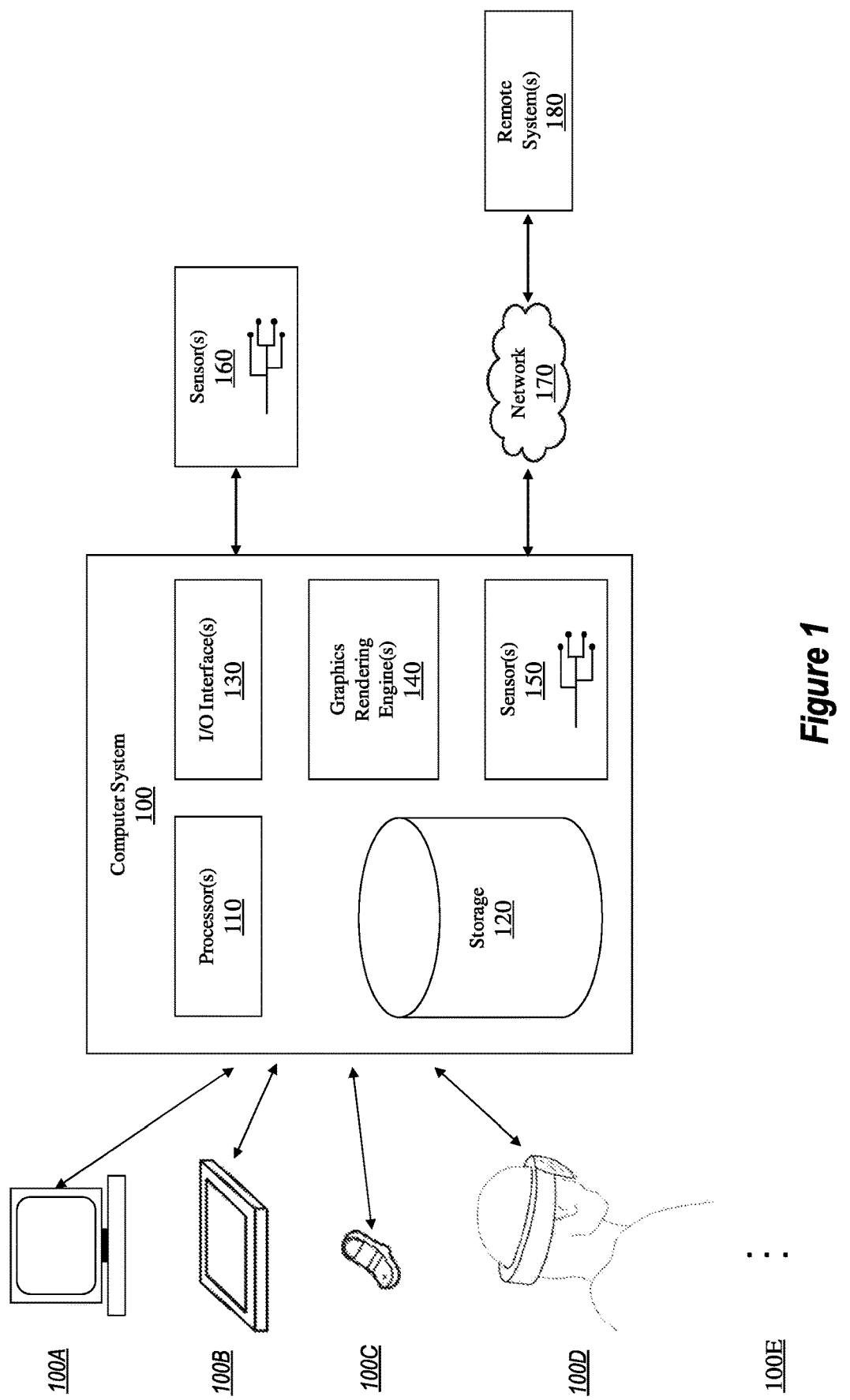
FIG. 1 illustrates a basic architectural view of a computer system that is able to perform the disclosed processes and methods.

As illustrated in FIG. 1, in its most basic configuration, a computer system 100 takes many different forms. For instance, FIG. 1 illustrates the computer system 100 as a desktop (or laptop) computer 100A, a tablet 100B, a cellphone 100C, or a head mounted device 100D that includes a HMD. Although FIG. 1 illustrates a broad array of computing devices, the current embodiments are not limited solely to those that are illustrated in FIG. 1. As a result, the ellipses 100E demonstrates that any type of computing device is available for use by the present embodiments.

The computer system 100 typically includes at least one processing unit 110 and storage 120. The storage 120 may be physical system memory, which may be volatile, non-volatile, or some combination of the two. The term "memory" may also be used herein to refer to non-volatile mass storage such as physical storage media. If the computing system is distributed, the processing, memory, and/or storage capability may be distributed as well. As used herein, the term "executable module," "executable component," or even "component" can refer to software objects, routines, or methods that may be executed on the computing system. The different components, modules, engines, and services described herein may be implemented as objects or processors that execute on the computing system (e.g. as separate threads).

Embodiments of the present invention may comprise or utilize a special purpose or general-purpose computer including computer hardware, such as, for example, one or more processors (such as processor 110) and system memory (such as storage 120), as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions in the form of data are physical computer storage media. Computer-readable media that carry computer-executable instructions are transmission media. Thus, by way of example, and not limitation, embodiments of the invention can comprise at least two distinctly different kinds of computer-readable media: computer storage media and transmission media.

Computer storage media comprise hardware, such as RAM, ROM, EEPROM, CD-ROM, solid state drives (SSDs) that are based on RAM, Flash memory, phase-change memory (PCM), or other types of memory, or other optical disk storage, magnetic disk storage or other magnetic storage devices, or any other hardware medium which can be used to store desired program code means in the form of computer-executable instructions, data or data structures and which can be accessed by a general purpose or special purpose computer.

As also shown in FIG. 1, the computer system 100 comprises various different components including I/O interface(s) 130, graphics rendering engine(s) 140, and one or more sensors 150. The computer system 100 may also be connected (via a wired or wireless connection) to external sensors 160 (e.g., one or more remote cameras, accelerometers, gyroscopes, acoustic sensors, magnetometers, etc.). Further, the computer system 100 may also be connected through one or more wired or wireless networks 170 to remote systems(s) 180 that are configured to perform any of the processing described with regard to computer system 100.

During use, a user of the computer system 100 is able to perceive information (e.g., a computer-generated scene) through a display screen that is included within the I/O interface(s) 130. The I/O interface(s) 130 and sensors 150/160 also include gesture detection devices, eye trackers, and/or other movement detecting components (e.g., cameras, gyroscopes, accelerometers, magnetometers, acoustic sensors, global positioning systems ("GPS"), etc.) that are able to detect positioning and movement of one or more real-world objects, such as a user's hand, a stylus, and/or any other object(s) that the user may interact with while being immersed in the scene (i.e. a mixed-reality environment).

In some instances, the positioning and movement of the user and the objects are continuously monitored. This monitoring specifically detects any variation in the position and the movement of the objects, such as a detected change in position, velocity, orientation, or acceleration. These movements can be absolute movements and/or relative movements, such as compared to a relative positioning of the HMD, and such that movements/positioning of the HMD will be calculated into the relative movements/positioning of the objects as they are presented in the scene.

The graphics rendering engine 140 is configured, with the processor(s) 110, to render one or more virtual objects within the computer-generated scene. This rendering includes hand occlusions, or other types of occlusions, that are mapped to the relative positions of real world objects. As a result, the virtual objects accurately move in response to movement of the real-world objects. The graphics rendering engine 140 is also configured to render one or more occlusions that are purely virtual (without being mapped to real world objects) but which are, nonetheless, positioned and moved responsively to user input as the user interacts within the scene.

The graphics rendering engine(s) 140, which may include one or more GPUs, is configured to render the occlusions (i.e., virtual objects) with certain display properties. These properties include coloring, transparency or opaqueness, texturing, edge definition (e.g., thickness and/or sharpness vs. blurring and/or feathering), size, and so forth. When certain movement thresholds are detected for the occlusion, then one or more combinations of the display properties for the occlusion will be modified (at least while the detected movement meets or exceeds the movement thresholds).

The movement thresholds can include any combination of the following: 1) detected actual movements of the real-world object associated with the occlusion, 2) detected animation movement of the virtualized occlusion, and/or 3) detected variance or lag between the real-world movement and the animated movement. The detected movements are associated with velocity and/or acceleration attribute values. These values are detected, measured, and/or calculated by the sensors 150 and/or processors 110 of the computer system 100 to determine when predetermined thresholds have been met and/or exceeded.

In some embodiments, the same absolute movement thresholds are associated with all types of movements. For instance, a certain velocity, acceleration, or lag associated with an occlusion will be sufficient to trigger a change in the display properties of the occlusion. This change may be triggered regardless of the specific type of detected movement. In other embodiments, different types of movements (i.e., different movements within the six degrees of freedom, including surge, heave, sway, pitch, roll, and yaw) are associated with different movement thresholds. For instance, a particular rotational acceleration will trigger a first threshold that is different than a lateral acceleration.

In some instances, there are at least two or more separate threshold limits for one or more of the different movement types. For instance, at a first acceleration metric, the first threshold is met. At a second acceleration metric, which is greater or less than the first acceleration metric, a second threshold is met. In some instances, one or more separate velocity thresholds are set for each of one or more types of movement. The appearance of the occlusion will dynamically change in response to each of the different thresholds being met, such as by changing the display attributes of the occlusion.

The various thresholds and movement attribute types are mapped in stored data structures in the storage 120 of the computing system 100 and/or in one or more remote system(s) 180.

Some disclosed embodiments include the GPU(s) 140 communicating with the storage to determine when and how to gradually modify the appearance of the occlusion correspondingly to different detected changes in the movement attribute(s) that are associated with the occlusion. In such embodiments, the display attributes/properties are continuously changed/scaled according to a continuously changing movement attribute (such that there are no discrete levels). For instance, the levels of transparency and/or edge feathering for an occlusion may be associated with many different corresponding magnitudes of velocity and/or acceleration associated with the occlusion (even when comprising movement of the real-world object) and/or lag associated with rendering an animation of the occlusion.

A "network," like the network 170 shown in FIG. 1, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. The computer system 100 will include one or more communication channels that are used to communicate with the network 170.

Transmissions media include a network that can be used to carry data or desired program code means in the form of computer-executable instructions or in the form of data structures. Further, these computer-executable instructions can be accessed by a general purpose or special purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems that are linked (either by hardwired data links, wireless data links, or by a combination of hardwired and wireless data links) through a network, each perform tasks (e.g. cloud computing, cloud services and the like). In a distributed system environment, program modules may be located in both local and remote memory storage devices.

Late Stage Reprojection ("LSR")

One issue with generating a realistic mixed-reality environment relates to the latency, or amount of time, in which images of world-locked virtual objects corresponding with a particular pose of an HMD are displayed to an end user of the HMD. For example, if too much time lapses between the time the end user's head turns away from the particular pose and the time an image of a virtual object is displayed based on the next pose, then the virtual object will appear to drift away from its intended location within the mixed-reality environment (i.e., the image may not appear to be aligned with an intended real-world location or object). Consequently, HMDs can also include technology for generating and displaying some virtual objects at a frame rate that is greater than a rendering frame rate of other virtual objects.

Rendering virtual objects at an increased frame rate significantly improves a scene's stability. The displayed objects (i.e. virtual objects) may include late stage graphical adjustments of pre-rendered scenes (i.e., forward predicted scenes that are rendered at a certain rendering frame rate) in order to incorporate higher frequency pose estimates. The rendering frame rate may correspond with the minimum time to render images associated with a pose of a HMD. To accomplish that objective, the HMD may perform one or more of the following: 1) determine a predicted pose associated with a future position and orientation of the HMD (e.g., a predicted pose of the HMD 10 ms or 20 ms in the future), 2) generate a pre-rendered image based on that predicted pose, 3) determine an updated pose associated with the HMD subsequent to generating the pre-rendered image or concurrent with the pre-rendered image being generated, 4) generate an updated image based on the updated pose and the pre-rendered image, and 5) display the updated image on the HMD. The updated image may be generated via a homographic transformation and/or a pixel offset adjustment of the pre-rendered image. In some cases, the updated image may be generated by circuitry within the display. Further detail on these functionalities will be provided later in this disclosure.

The predicted pose may be determined based on 1) a current position and orientation of the HMD and 2) an acceleration and a velocity of the HMD immediately prior to determining the predicted pose (e.g., by extrapolating the predicted pose based on movement of the HMD 5 ms, 10 ms or another predetermined distance prior to determining the predicted pose). The updated pose may be determined based on updated pose information that is provided to a pose tracker at a higher frequency than the rendering frame rate (e.g., by acquiring data from various pose tracking instrumentation, such as accelerometers, gyroscopes, etc.).

This updated pose information may be generated using a low-latency inertial measurement unit (IMU) or combination of IMU and camera-based pose tracking. The updated image may comprise an image rotation, translation, dilation (e.g., stretching or shrinking), shifting, or tilting of at least a portion of the pre-rendered image in order to correct for differences between the predicted pose and the updated pose (e.g., to compensate for an incorrect pose prediction when generating the pre-rendered image).

Even further, the updated image may be generated via a homographic transformation of the pre-rendered image. In some cases, the homographic transformation may comprise an affine transformation. The updated image may be generated using a pixel offset adjustment or a combination of homographic transformations and pixel offset adjustments. In some cases, the homographic transformations and/or pixel offset adjustments may be generated downstream from the core rendering pipeline (e.g., using a controller or processor integrated with the HMD). In other cases, the pixel offset adjustments may be performed using a display that incorporates shift registers or other circuitry for allowing the shifting of pixel values within a pixel array of the display (e.g., similar to the operation of a charge-coupled device).

The updated images include late stage graphical adjustments of forward predicted rendered images and may be generated using various image reprojection techniques of varying computational complexity. The image reprojection techniques may include per pixel reprojection (e.g., where each pixel of a rendered image is reprojected based on an updated pose), multi-layered homography (e.g., where multiple rendered images associated with multiple layers within a 3D scene are used to generate the composite updated image), single layer homography (e.g., where a single rendered image associated with a single layer within a 3D scene is used to generate the updated image), affine homography, or pixel offset based adjustments.

Additional details regarding LSR processing can be found in U.S. Pat. No. 9,514,571, issued Nov. 16, 2016 and entitled "Late Stage Reprojection", and U.S. patent application Ser. No. 15/227,453, filed Aug. 3, 2016 and entitled "Late Stage Reprojection," the disclosures of which are incorporated herein by reference.

Although prior systems do support LSR adjustment, these systems fail to optimize that processing in an efficient manner. As a result, these systems suffer many handicaps associated with battery longevity. Disclosed embodiments can be used to help resolve some of these problems by performing selective LSR adjustments for multi-layered scenes.

Multi-Layer Computer-Generated Scenes

Figure 2:
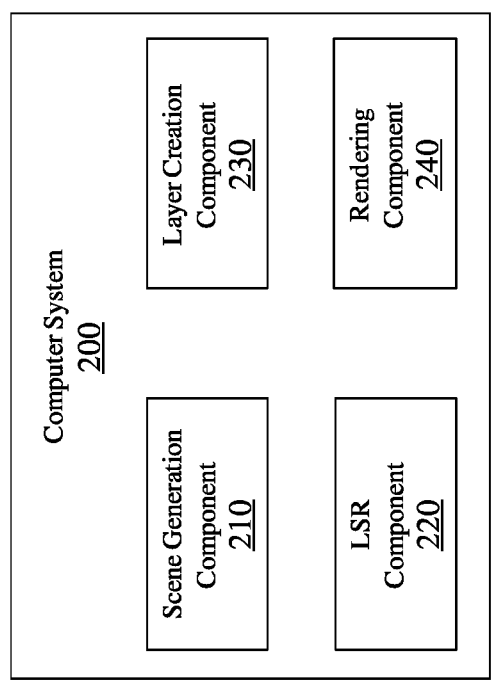
FIG. 2 illustrates another embodiment of a computer system that is able to perform the disclosed processes and methods.

Attention will now be directed FIGS. 2-12. Briefly, FIG. 2 illustrates an exemplary computer system that includes various components for optimizing LSR processing on computer-generated scenes that include multiple layers. FIGS. 3-12 expound on various functionalities that are available in the present embodiments.

As indicated above, FIG. 2 illustrates a computer system 200 that includes various components (e.g., a scene generation component 210, a LSR component 220, a layer creation component 230, and a rendering component 240). The computer system 200 is analogous to the computer system 100 presented in FIG. 1. In some embodiments, the computer system 200 is configured as a specialized set of one or more processors (e.g., GPUs). Additional attributes of the computer system 200 will also be discussed in connection with the remaining figures.

In particular, the computer system 200 is able to create and render a computer-generated scene. This scene can be a mixed-, augmented-, or virtual-reality scene. As discussed previously, this scene is generated based on information that was previously acquired by one or more hardware components of the computer system (e.g., IMU instrumentation, accelerometers, gyroscopes, magnetometers, depth sensors, camera, infrared sensors, etc.).

Some embodiments generate this scene in response to a first predicted pose of a part (e.g., perhaps the HMD) of the computer system. This first predicted pose is different than a previously acquired actual determined pose of the part of the computer system. In an effort to reduce how often data is acquired from hardware components (which process places a toll on the computer system's battery life), embodiments of the present invention augment the actual pose data with predicted, or computer-estimated, pose data. By performing this augmentation process, how often (i.e. the frequency) pose data is acquired from the hardware components can be lessened. This augmentation process significantly lowers power consumption. To further clarify, suppose the computer system collects pose data from the various hardware components (e.g., the IMU instrumentation discussed earlier) at a certain frequency. The present embodiments reduce how often this real/actual data is collected by augmenting the actual pose data with predicted pose data. Accordingly, as discussed throughout this disclosure, the present embodiments are able to predict the pose of a computer device based on 1) previously acquired actual pose determinations and 2) estimations regarding a current and/or future behavior of the user (e.g., by tracking body movement or other characteristics).

Figure 3:
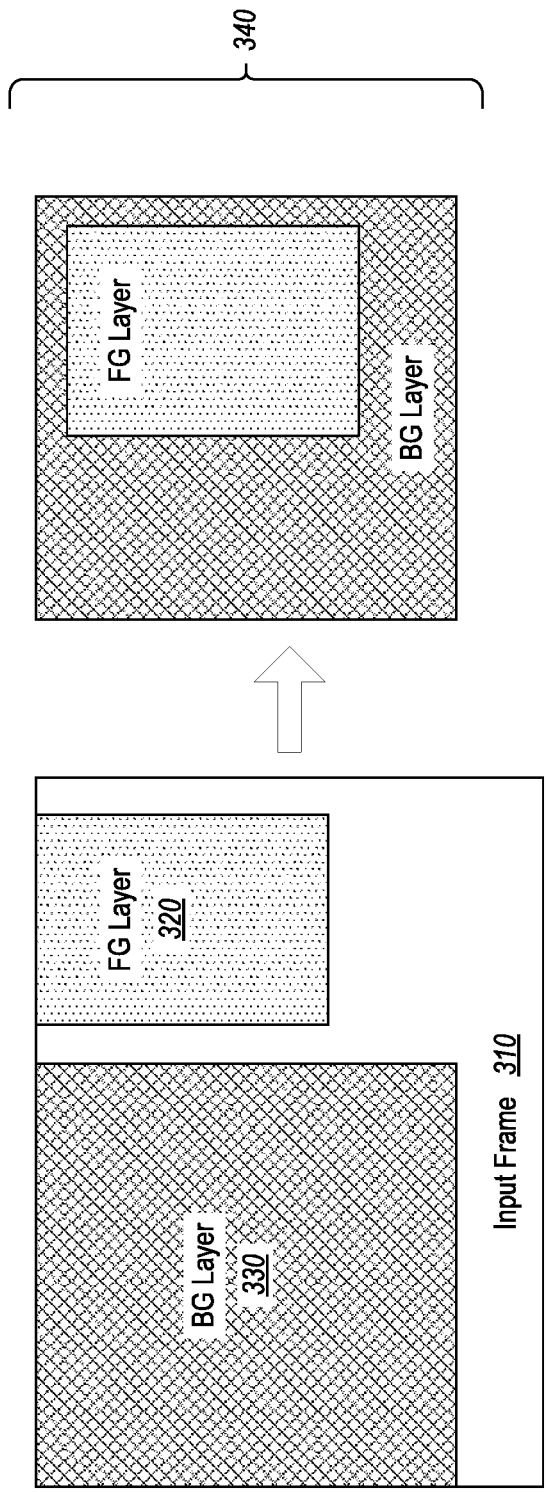
FIG. 3 illustrates a high-level overview of a multi-layered scene.

Continuing the discussion, the scene generation component 210 is able to create a scene that includes a plurality of input frames, such as the input frame 310 shown in FIG. 3. Use of the term "input frame" correlates with the term "scene;" meaning, the scene is actually comprised of a plurality of input frames that are displayed to a user wearing a HMD. As further shown in FIG. 3, the input frame 310 includes a foreground layer 320 ("FG layer") and a background layer 330 ("BG layer"). The FG layer 320 and the BG layer 330 are created by the layer creation component 230. In some situations, the FG layer 320 is rendered according to a first resolution while the BG layer 330 is rendered according to a second resolution. By way of example, the FG layer 320 may include an object (e.g., a tree) that appears to be visually closer to a user while the BG layer 330 may include a landscape (e.g., mountains in the distant background) that appears to be further away from the user. Because the BG layer 330 includes content that appears to be visually "further away" from the user, the content in the BG layer 330 can be rendered at a lower resolution.

In other situations, the computer system 100 supports foveated rendering. In view of this foveated rendering, the FG layer 320 may be placed in the higher resolution area (i.e. the fovea area) while the BG layer 330 may be placed in a much lower resolution area (e.g., an edge or peripheral region of the scene).

The LSR component 220 is able to perform LSR processing on the FG layer 320 and the BG layer 330. In some instances, the LSR processing that is applied to the FG layer 320 is different than the LSR processing that is applied to the BG layer 330. This difference in LSR processing between the FG layer 320 and the BG layer 330 can be due to a wide variety of reasons. By way of example and not limitation, the difference may be due to a difference in determined depth between the FG layer 320 and the BG layer 330. Movement of the HMD may also affect positioning/rendering of the FG component differently than the positioning/rendering of the BG components.

At this point, an example will be helpful. Using the example from above, suppose the scene that is being presented to the user includes a tree that is nearby and a distant mountainous landscape. Now, suppose the user moves position or otherwise changes her orientation. In response to the user's change in position, the mixed-reality scene will need to be updated. Here, it is worthwhile to note that the change in visual effect for the tree, which is much closer to the user, will be significantly larger than any change for the distant mountainous landscape because of the difference in perceived depth. As a result, the LSR processing for each layer may be different.

After the LSR processing is applied to the various layers of the scene (e.g., the FG layer 320 and the BG layer 330), the computer system composites the layers together to form a unified layer, such as the unified layer 340 in FIG. 3. In other words, the FG layer 320 and the BG layer 330 (after undergoing LSR processing) are composited together to form the unified layer 340. To ensure that the layers are properly visualized in the scene (e.g., to ensure that the layers are visualized with correct depth and orientation with regard to one another), the computer system 200 also applies one or more transformations to one or more of the layers. These transformations may be applied either during the LSR processing or during the composite processing. By way of example, one layer may need to be resized (i.e. dilated), rotated, skewed, or otherwise manipulated, which may not be required for the other layer(s) in the unified scene. To accomplish this selective manipulation, the computer system 200 applies the appropriate type of transformation to enable the layer to be properly rendered. Some of these transformations include a homographic transformation, an invertible image transformation, an affine transformation, a pixel offset adjustment, depth processing transformations, and/or a matrix transformation. After compositing the layers together, the rendering component 240 renders the unified layer 340 on a HMD.

While FIG. 3 illustrated an abstract visualization of a multi-layered scene, FIGS. 4-7 illustrate a specific implementation.

Figure 4:
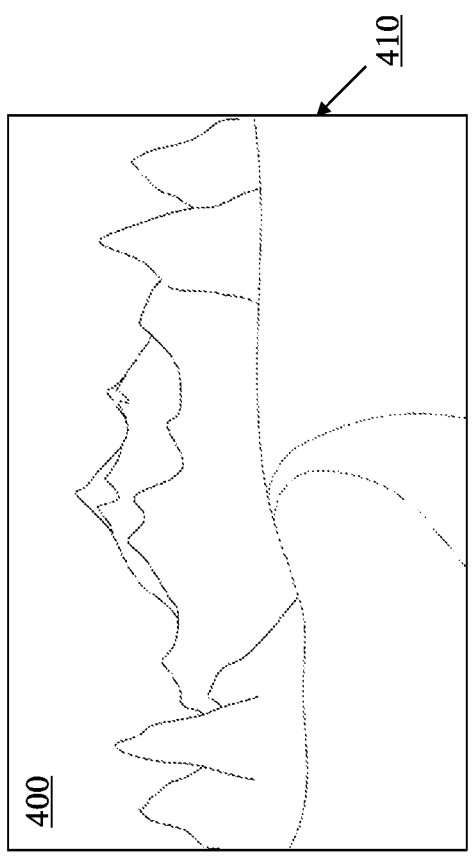
FIG. 4 provides a realistic depiction of one layer that can be used in a multi-layered scene.

In particular, FIG. 4 illustrates a first layer 400 of a computer-generated scene. This first layer is analogous with the BG layer 330 in FIG. 3. This first layer 400 is illustrated as being bounded by a bounding region 410. This bounding region 410 relates to an area that is viewable by a user wearing a HMD. Notably, however, the computer-generated scene is not restricted to only a single point of view. Rather, as the user moves positions or otherwise changes orientation, the view that is displayed on the HMD will change in relation to the HMD's orientation (e.g., new content will appear while other content will disappear in accordance with the user's movement). As a result, the first layer 400 and the bounding region 410 should not be used to characterize or otherwise limit the abilities of the computer system 200.

Figure 5:
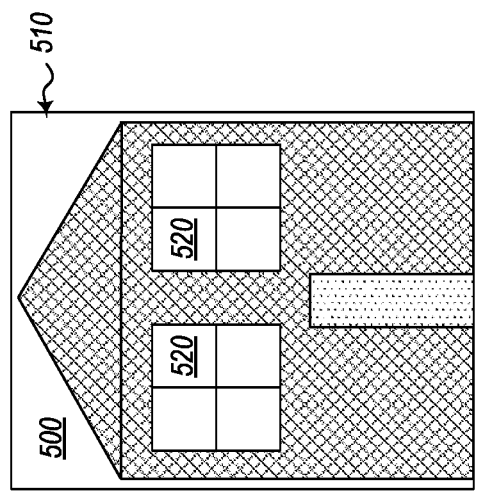
FIG. 5 provides another realistic depiction of a layer that can be used in a multi-layered scene.

Similar to FIG. 4, FIG. 5 illustrates a second layer 500 that can be visualized by the computer system 200. This second layer 500 is analogous to the FG layer 320 in FIG. 3. The second layer 500 is also illustrated as having a bounded region 510. Here, it is worthwhile to note that the second layer 500 is slightly different than the first layer 400 of FIG. 4. In particular, the second layer 500 includes one or more transparent portions 520. By transparent, it is meant that any content positioned underneath this transparent portion 520 will be viewable even though that underneath content is not a part of the second layer 500. As a result, after 1) the LSR processing of the second layer 500, 2) any transformations, and/or 3) the compositing processes are applied to the second layer 500 (and if the layer 500 is still disposed overtop another layer so as to overlap that other layer), at least some of the bottom layer will be visible through the transparent portions 520 of the second layer 500.

Figure 6:
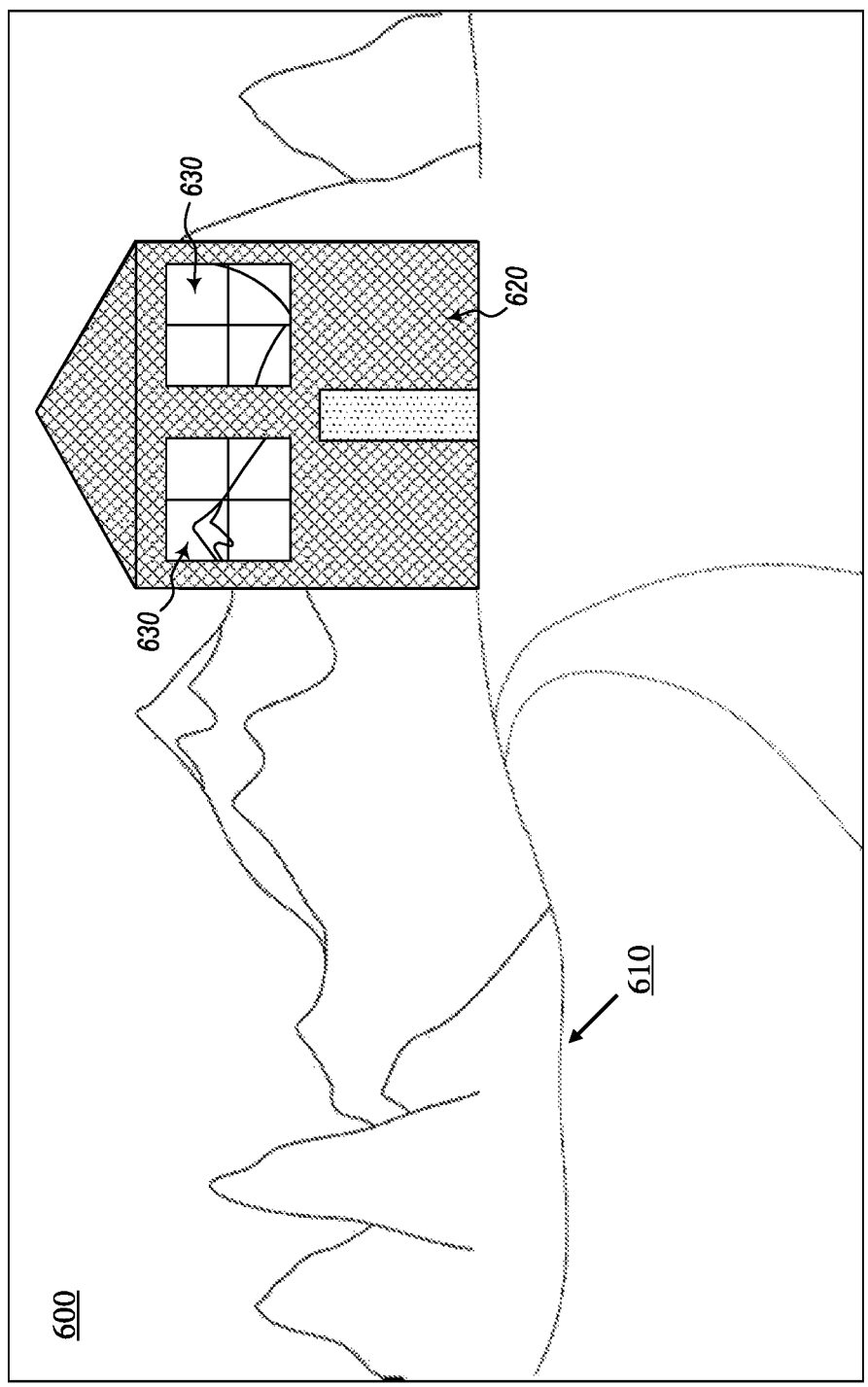
FIG. 6 illustrates a composite rendering of multiple layers.

FIG. 6 illustrates a multi-layered scene 600 presented as a unified, composite layer. This multi-layered scene 600 is created by the scene generation component 210. The multi-layered scene 600 includes a first layer 610, which is analogous to the first layer 400 in FIG. 4, and a second layer 620, which is analogous to the second layer 500 in FIG. 5. In other words, this unified layer 600 is a composite of multiple layers. As further illustrated in FIG. 6, the second layer 620 includes one or more transparent portions 630, which are analogous to the transparent portions 520 in FIG. 5. Here, it is worthwhile to note that a portion of the first layer 610 is viewable through the transparent portion 630 of the second layer 620. To clarify, the second layer 620 is a layer that has been placed on top of the first layer 610. As a result, the second layer 620 occludes, or obfuscates, various portions of the first layer 610. However, because the second layer 620 includes the transparent portions 630, certain portions of the first layer 610 are viewable through the transparent portions 630 of the second layer 620 (at least while the user is in this particular pose). If the user were to later change position or orientation, then other portions of the first layer 610 will become visible through the transparent portions 630 of the second layer 620. Which portions are visible are directly related to the user's pose.

Figure 7:
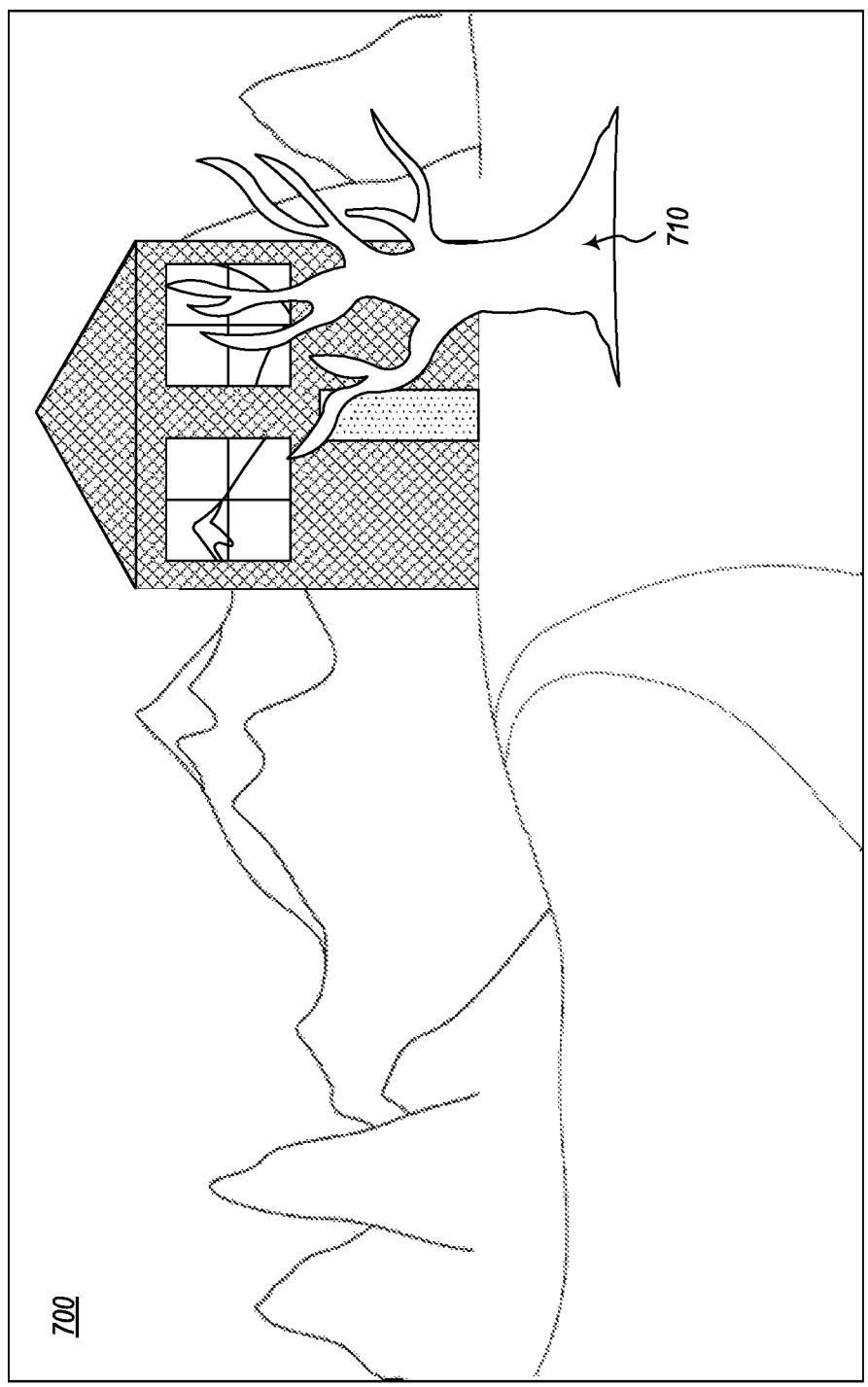
FIG. 7 illustrates another composite rendering of multiple layers.

FIG. 7 is similar to FIG. 6 but includes an additional layer, layer 710. In particular, FIG. 7 illustrates a multi-layered scene 700 that is similar to the multi-layered scene 600 in FIG. 6. Now, however, the multi-layered scene 700 includes an additional layer, layer 710 (i.e. the tree). Layer 710 is positioned to overlap the other layers in the multi-layered scene 700. Notably, a portion of layer 710 occludes some of the transparent portions of a bottom layer (i.e. the house). As a result, layer 710 occludes various portions of the other layers (e.g., the tree covers the window, the window covers the mountain, but the mountain is viewable through the window because the window is transparent, but the tree also covers a part of the mountain).

As discussed above, the various layers may each undergo the same or different LSR processing, depending on the LSR processing being performed and the detected movements of the HMD. In a worst-case scenario, all of the pixels in all of the layers undergo LSR processing. Using FIG. 3 as an example, the worst-case scenario would occur if all of the pixels of the BG layer 330 and all of the pixels of the FG layer 320 were to undergo LSR processing.

In an effort to improve the efficiency of the LSR processing, some of the present embodiments pre-filter at least some of the pixels in the various layers of a multi-layered scene. One method of pre-filtering pixels is by using a pixel mask. A pixel mask can be defined per row and column on the top, bottom, left, and right edges of a particular layer. As alluded to in the above discussion, this pixel mask can be used to eliminate processing on pixels, some of which may not contribute significantly to image quality (e.g., pixels that are located on an edge region of the display). This pre-filtering process allows some of the LSR processing to be skipped for individual pixels and even for large stretches of pixels. This pre-filtering process is generally visualized in FIG. 8.

Figure 8:
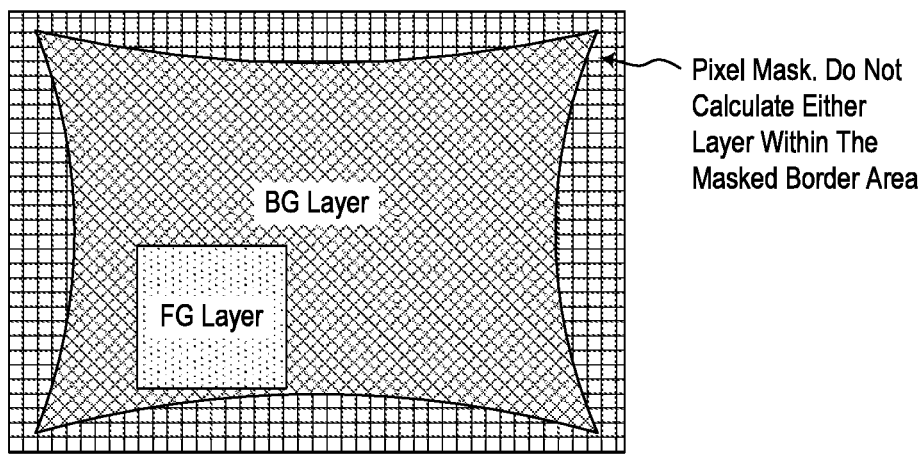
FIG. 8 illustrates an example of how a pre-filter can be applied to certain pixels in a layer.
Figure 9:
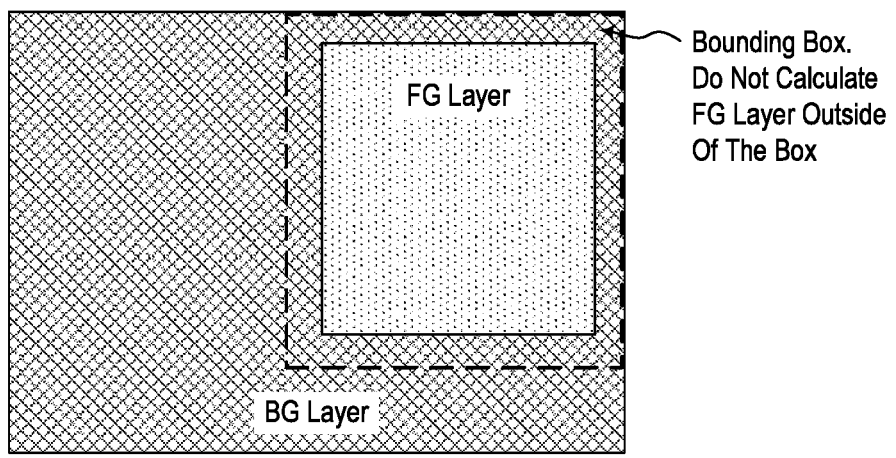
FIG. 9 illustrates an example of how a layer is constrained within a bounding region.
Figure 10:
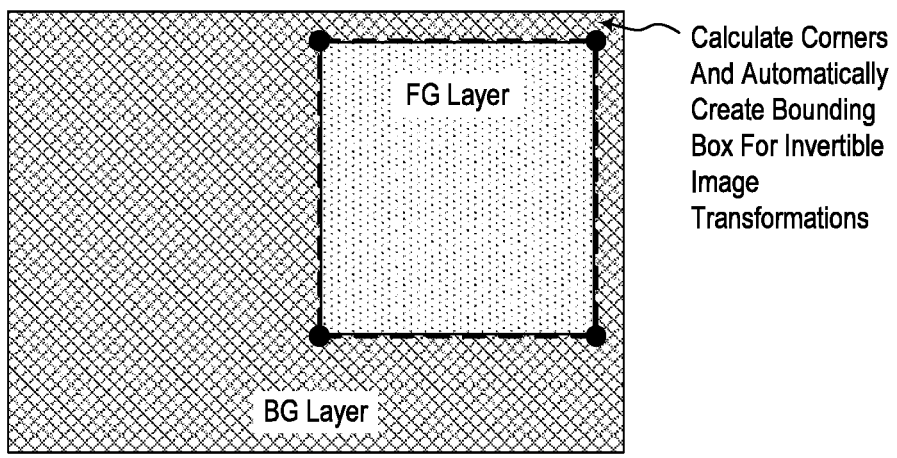
FIG. 10 illustrates another example of how a layer is constrained within a bounding region.

In particular, FIG. 8 shows that a pixel mask can be applied to one (or more) layers (e.g., the BG layer 330 of FIG. 3). By applying the pixel mask, LSR processing does not need to be performed, or rather can be omitted/skipped, on the pixels that were identified by the pixel mask, operated on by the pixel mask, or otherwise corresponding to the pixel mask.

While FIG. 8 disclosed the use of a pixel mask, other types of operations can also be used to pre-filter pixels. By way of example and not limitation, a vector mask can also be used to pre-filter some of the pixels (e.g., identify pixels to omit from LSR).

Other embodiments reduce or eliminate LSR computing at every pixel location by applying a bounding box around certain layers. This bounding box functionality is visualized in FIG. 9. In particular, this bounding box is used to define an area that fully encompasses a certain layer (or a sub-region within a layer) within an output image (i.e. a rendered scene). When using this bounding box, the various embodiments eliminate all calculations outside of the box as the output image changes (e.g., as the user changes position or orientation and the scene adjusts accordingly). As illustrated in this passage, a bounding box is used to identify and isolate a sub-region within a particular layer. After this sub-region is isolated, then the computer system 200 applies LSR processing to this sub-region while foregoing applying LSR processing to the remaining regions in that layer. As a result, the computer system 200 selectively determines which areas of a layer should have LSR processing applied thereon.

As discussed earlier, when a user changes position or orientation, the layers will need to be adjusted accordingly to reflect that change in position or orientation. By way of example, if the user moves to her right, the various layers will need to be adjusted to reflect the user's new viewpoint. Here, an example will be insightful. Suppose the user is viewing the multi-layered scene 700 of FIG. 7. As the user moves to her right, the user's view of the tree, house, and mountain landscape will all change. In particular, new areas of the tree and house will likely be viewable. The user's view of the tree and house relative to the mountain landscape will also change. In contrast, the view of the mountainous landscape, which is very remote from the user, will likely not change at all, and if it does, the change will quite likely be extremely small so as to be unnoticeable. Because the tree is closer to the user than the house, more visual changes will be noticeable with regard to the change of perspective for the tree than will be noticeable with regard to the house. Accordingly, the computer system supports the application of different LSR processing on the different layers and which may be triggered by detecting certain movement thresholds for the different layers. Independent triggers may apply to separate threshold determinations for each layer.

Continuing with the discussion, to perform this adjustment in response to the user's change in position, the computer system 200 selectively applies various transformations to the layers. These transformations are applied during the LSR processing and/or during a later composite process. One such transformation, as briefly mentioned earlier, is an invertible image transformation. This type of transformation determines the corners of a layer (e.g., perhaps using the bounding box of FIG. 9) using image resolution techniques. This transformation is then inverted to determine the point in the unified layer (i.e. the output image) that corresponds to the upper left corner of the input image, as is currently shown in FIG. 10. Similar calculations are performed for determining the other corners. Once the layer is identified, then the layer can be manipulated in a variety of ways (e.g., stretched, shrunk, skewed, etc.). As discussed earlier, other types of transformations include homographic transformations, affine transformations, pixel offset adjustments, depth processing transformations, and matrix transformations.

Figure 11:
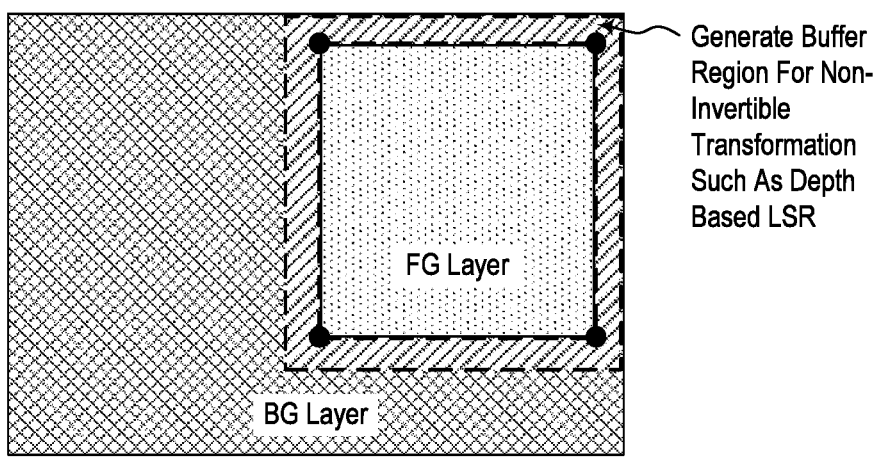
FIG. 11 illustrates the use of a buffer region that is usable during LSR processing.

Here, it is worthwhile to note that not all transformations are easily invertible. For example, large scale movements can be performed with a matrix transformation. However, smaller adjustments can be done using other transformations (e.g., depth processing transformations). To account for these transformations, some embodiments impose a buffer region around the previously generated bounding box. This buffer region is illustrated in FIG. 11 and can be used to help blend the various layers together to make a cohesive, visually appealing unified layer.

Figure 12:
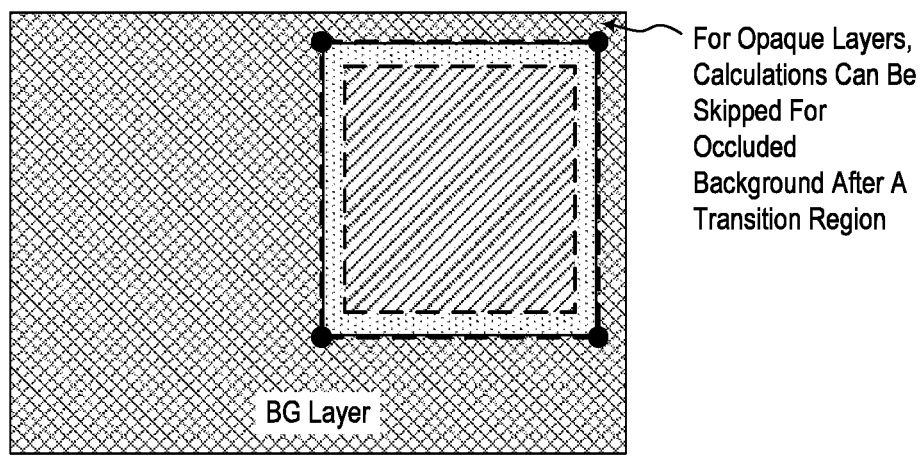
FIG. 12 illustrates how the amount of LSR processing can be reduced in various situations.

In many cases, such as when a HMD supports foveated rendering, a background layer will be completely occluded by a foreground layer after a small amount of blending is performed. The present embodiments capitalize on situations such as these by reducing, or even entirely eliminating, the amount of processing that is applied to those occluded portions. For example, FIG. 12 shows a foreground layer that is opaque and that occludes a portion of the bottom BG layer. For the portions of the bottom layer that are obscured by the opaque regions of a top layer, LSR calculations can be skipped and battery consumption can be reduced.

Having just discussed a computer system that optimizes LSR processing on a multi-layered scene, the disclosure will now present various exemplary methods for optimizing LSR processing. Notably, the following discussion refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Selective Application of Reprojection Processing on Layer Sub-Regions

FIG. 13 illustrates an exemplary method 1300 that is performed by a computer system, such as the computer system 200 of FIG. 2. In particular, the method 1300 includes an act (act 1310) of generating a scene that includes one or more layers.

Here, it is worthwhile to note that in some instances, an entire layer may be comprised of only a single element such that the element is the layer. Using FIG. 5 as an example, the entire layer 500 is comprised of only the single house element. In other instances, however, a layer may be comprised of multiple elements. By way of example and not limitation, FIG. 4 illustrates that layer 400 includes a mountainous landscape, a road, the sky, and perhaps a grassland. Here, the mountainous landscape may be considered a distinct element, the road may be considered a distinct element, etc. Therefore, in some instances, the layer 400 is comprised of multiple distinct elements. In other embodiments, however, there is no such distinction between elements in a layer.

In some embodiments, the scene is generated based on various poses of a portion (e.g., the HMD) of a computer system. To clarify, the poses include both actual poses determined by IMU instrumentation as well as predicted poses determined by estimated behavior and anticipated movement. Here, the scene generation component 210 generates the scene in the manner previously described. Further description of this functionality will be presented later in this disclosure.

Some embodiments configure this scene for foveated rendering. In particular, these embodiments utilize eye tracking technology to track the user's eye movements. Then, these embodiments render the scene so that at least one of the layers is displayed as being near a fovea of the user's eye while other layers are not displayed as being near the fovea of the user's eye. Correspondingly, if the embodiments distinguish between elements within a layer, then the elements are also displayed according to foveated rendering techniques.

The method 1300 also includes an act (act 1320) of identifying a sub-region within the one or more layers. This sub-region is distinguished from at least one other region in the one or more layers. Here, the layer creation component 230 manipulates and otherwise distinguishes sub-regions within the various layers.

In some embodiments, the process of identifying this sub-region also includes identifying 1) a particular element within the one or more layers and 2) a buffer boundary around the particular element. Therefore, in these embodiments, the sub-region includes both the element itself as well as the buffer boundary around the element. In contrast, other embodiments do not include such a buffer boundary around the sub-region.

In the example from above, the layer 400 in FIG. 4 is comprised of multiple elements (e.g., the mountainous landscape element, the road element, etc.). Some embodiments select an entire element (e.g., the road element) to serve as the sub-region. Alternatively, however, the identified sub-region can just be a generalized layer portion without any particular relationship to an element.

In some embodiments, the particular element is identified in response to detecting a particular movement threshold has been met or exceeded for the element relative to the HMD relative, which has not been met for the relative movement of other elements/layers relative to the HMD.

The method 1300 then includes an act (act 1330) of isolating the identified sub-region from the at least one other region of the one or more layers. Similar to the above step, the layer creation component 230 also performs this act. This isolation is performed in a variety of ways. For example, this isolation is performed by applying a pixel mask or a vector mask to the one or more layers. As detailed above, a buffer region can also be applied around this isolated sub-region. This buffer region is created in the manner described previously in this disclosure.

Continuing with the example from above, suppose the road element is selected as the sub-region. This road element is then distinguished from the other regions in the layer 400 (e.g., the other regions at least include the mountainous landscape element). To distinguish the road element, the embodiments isolate the road element from the other regions by using a pixel mask, vector mask, bounding box, etc.

Lastly, FIG. 13 shows an act (act 1340) of applying late stage reprojection processing to the isolated sub-region while refraining from applying late stage reprojection processing to the at least one other region of the one or more layers. By way of example, the LSR component 220 performs the LSR processing in the manner previously described. In some embodiments, the LSR processing includes one or more transformations for transforming the one or more layers or the elements within the one or more layers. These transformations include a homographic transformation, an affine transformation, an invertible image transformation, a pixel offset adjustment, a depth processing transformation, a matrix transformation, or any other kind of image transformation (stretch, skew, dilate, rotate, etc.). Further, the one or more transformations are applied to the one or more layers (or the elements within those layers) in response to a certain predicted pose of a portion (e.g., the HMD) of the computer system. Here, it is worthwhile to note that in some multi-layered scenes, LSR processing is applied to all of the pixels in one layer while LSR processing is applied to only a subset of pixels in a different layer. In other situations, however, LSR processing is applied to all of the pixels in all of the layers. This situation is often the worst-case scenario.

Continuing with the example from above, after the road element is selected for isolation, the embodiments perform LSR processing on that road element. For example, suppose the user changes her position or orientation in some manner (e.g., perhaps the user goes from a standing position to a sitting position). The portions of the road furthest from the user will likely not have changed much in perspective or view. However, the portions of the road closest to the user will likely have changed significantly in perspective in response to the user's change in position, thereby exceeding a movement threshold in total distance and/or acceleration. In response to this new pose, these embodiments perform LSR processing on the identified element (e.g., the road or particular portion of the road).

As indicated above, this LSR processing may also include the selective application of various transformations. Here, certain transformations will need to be applied to the road element to ensure that its visualization is properly rendered in response to the user's change in position. For instance, the portion of the road nearest the user will likely have to be stretched, skewed, or otherwise manipulated to ensure that the road is properly aligned and perceived by the user. As a result, the LSR processing that is applied to the identified sub-region (e.g., the road element in layer 400) may be different than the LSR processing that is applied to the remaining regions within that layer (e.g. perhaps no LSR processing was applied to the mountainous landscape element because that element is perceived to be very remote from the user and will change very little in response to user position changes).

In scenes that include multiple layers, a portion of one layer (e.g., a top layer) will overlap a portion of a bottom layer. As a result, the portion of the top layer obfuscates an obfuscated portion of the bottom layer. In such multi-layered scenes, the identified sub-region may be included within the portion of the top layer that obfuscates the obfuscated portion of the underneath layer. Here, it is worthwhile to note that the identified sub-region, in some instances, will include a transparent portion (e.g., the transparent portion 630 from FIG. 6). In these situations, the portion of the underneath layer that is situated underneath the transparent portion of the sub-region will be viewable through the transparent portion, even after LSR processing is applied.

Accordingly, the embodiments support the selective application of LSR processing on layer sub-regions of a multi-layered scene.

Selectively Applying Reprojection Processing to Multi-Layer Scenes

Figure 14:
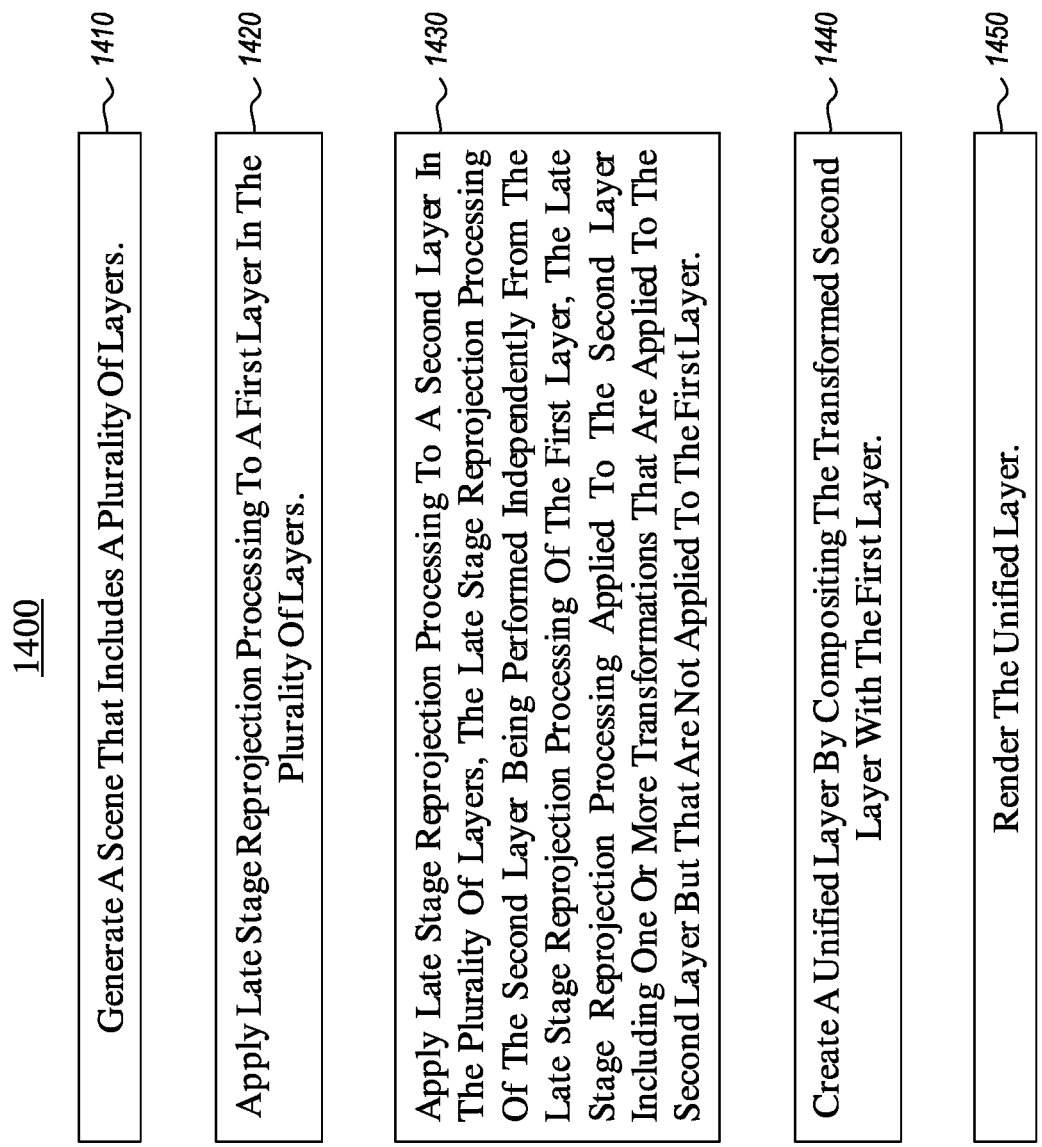
FIG. 14 illustrates another exemplary method for optimizing LSR processing.

FIG. 14 illustrates another exemplary method 1400 that is performed by a computer system, such as the computer system 200 in FIG. 2, where each scene element may comprise a different layer Initially, method 1400 includes an act (act 1410) of generating a scene that includes a plurality of layers. Here, the scene generation component 210 and the layer creation component 230 work in tandem to generate multi-layered scenes. Just as above, this scene may be included as part of a mixed-, augmented-, or virtual-reality scene.

In some embodiments, this scene is generated in response to various poses of a part (e.g., the HMD) of the computer system. These poses include 1) actual poses determined by IMU instrumentation and 2) predicted poses based on both user behavior (e.g., both historical and present behavior) and anticipated movement. When a predicted pose is generated, it is based on previous pose determinations. Further, predicted pose data is used to augment actual pose data so that the computer system reduces how often it acquires data from its hardware IMU instrumentation. By reducing how often data is actually collected, the embodiments prolong the computer system's battery lifespan.

Multiple pose determinations may be generated. For example, some embodiments generate a plurality of predicted pose determinations for a particular point in time (e.g, ten different pose estimates for time X), where each predicted pose determination is an estimate as to how the HMD will be positioned at that point in time. These embodiments assign a probability of realization to each of those predicted pose determinations (e.g., pose Y has a 52% likelihood of being realized, pose Z has a 35% likelihood of being realized, etc.). This probability is determined based on 1) historical behavior of the user, 2) the user's current movements, and/or 3) events that are presently occurring or that will soon occur in the scene (e.g., the software application determines that a new enemy will soon appear in the scene at a particular location and time and the software application estimates that the user will react to that new appearance by performing a certain movement). After the probability determinations are complete, the embodiments select the highest ranked predicted pose and continue with the next operations.

Other embodiments generate a plurality of predicted pose determinations in a different manner. Here, instead of generating a plurality of predicted pose determinations for a single point in time, these embodiments base successive predicted pose determinations on previous predicted pose determinations. To clarify, suppose the computer system collects actual pose data at a certain frequency, perhaps every 20 ms (this number is an example only and should not be considered as a limiting metric and may be more or less than 20 ms). Notably, however, the scene may need to be updated at a faster rate. As a result, these embodiments augment the actual pose data with predicted pose data. To do so, these embodiments generate a first predicted pose based at least partially on the actual pose data and render the scene based on that first predicted pose. Then, the embodiments generate a second predicted pose based at least partially on the first predicted pose and then render the scene based on that second predicted pose. This process continues, where a successive predicted pose is based on a previous predicted pose, until the computer system again acquires actual pose data. As a result, successive predicted poses are different than a previously acquired actual determined pose of the part of the computer system. In some situations (and in response to the various predicted poses), the LSR processing that is applied to the multiple layers in the scene is applied to all of the pixels of those layers. In other situations, however, the LSR processing is applied only to a subset of pixels within one or more layers.

Method 1400 also includes an act (act 1420) of applying LSR processing to a first layer in the plurality of layers. Here, the LSR component 220 applies the LSR processing to the layers. Notably, some embodiments apply LSR processing only to an identified subset of pixels within a particular layer (e.g., perhaps some of the pixels have been pre-filtered out of the layer in the manner described earlier in this disclosure) while other embodiments apply LSR processing to all of the pixels of the multiple layers.

Method 1400 also includes an act (act 1430) of applying LSR processing to a second layer in the plurality of layers. The LSR processing applied to this second layer is performed independently from the LSR processing of the first layer. Further, the LSR processing applied to the second layer includes one or more transformations (e.g., an invertible image transformation and/or a matrix transformation). These transformations are applied to the second layer but are not applied to the first layer. The different transformations that are applied to the first layer and the second layer may differ, based on detecting different attributes of the different layers and/or based on detecting that different movement thresholds have been met or not met for the different layers. Stored and accessed parameters define when different transformations should be applied to different layers.

Additional transformations can also be applied during a subsequent composite process that will be described later. Therefore, image transformations can be applied to the layers at various different times. Similar to the act above, the LSR component 220 applies this LSR processing. As a result, the LSR component 220 is able to apply different LSR processing to different layers at different times.

Here, it is worthwhile to note that a broad variety of transformations may be applied to the layers. In addition to the above-mentioned transformations (i.e. homographic transformations, affine transformations, invertible image transformations, depth processing transformations, pixel offset transformations, matrix transformations, etc.), the transformations also include 1) a translation, 2) a reflection, 3) a rotation, or 4) a dilation transformation. Various other transformations can be applied to change other characteristics of a layer. By way of example, suppose in response to a user's change in position, a new glare or reflection should be introduced into the scene (e.g., perhaps the computer system determines that sunlight should now reflect off of the window of the house in FIG. 5 and should be projected into the user's eyes). This new glare or reflection will impact how the user views the scene, particularly the color and transparency aspects of the various layers. As a result, the color or transparency of the various layers of the scene may need to be altered. Therefore, in addition to size transformations, the one or more transformations also include color and transparency transformations.

Method 1400 also includes an act (act 1440) of creating a unified layer. This unified layer is created by compositing the various layers together (e.g., the transformed second layer with the first layer). Here, the layer creation component 230 creates this unified layer.

Some embodiments perform this compositing by generating a buffer region around the second layer in the manner that was described previously in this disclosure. Further, compositing the transformed second layer with the first layer may cause the transformed second layer to overlap a portion of the first layer. As a result, the transformed second layer at least partially obfuscates a portion of the first layer. However, some of the layers may include a transparent portion(s). Because of this transparent portion(s), content that is underneath the transparent portion(s) is viewable through the transparent portion(s).

Finally, method 1400 includes an act (act 1450) of rendering the unified layer. This unified layer may be rendered on a HMD. Here, the rendering component 240 renders the unified layer.

Some embodiments support foveated rendering on the HMD so that the unified layer is rendered using foveated rendering techniques. To clarify, if the underlying computer system includes a HMD, then the rendering of the unified layer is performed by rendering the unified layer on the HMD.

Although not shown in FIG. 14, other embodiments include acts of pre-filtering pixels from the various layers. For example, some pixels of the first layer may be pre-filtered from other pixels of the first layer. Alternatively, some pixels of the first layer may be pre-filtered from pixels of a different layer (e.g., in the case of a unified, composite layer). This pre-filtering process is performed by applying a pixel mask or a vector mask. In these embodiments, at least some of the pixels that are pre-filtered are identified as being edge pixels. These edge pixels are determined to contribute less to scene quality than non-filtered or non-edge pixels. Because these pixels contribute less to scene quality, the embodiments optimize battery life by skipping LSR processing on these pixels.

Other embodiments generate additional predicted poses of the part (e.g., the HMD) of the computer system. These embodiments create a new unified layer by again compositing the second layer with the first layer. In some instances, the portion of the first layer that was previously viewable through a transparent portion of the second layer is now obfuscated in response to the orientation changes associated with the predicted next pose. Now, a new portion of the first layer that was not originally viewable through the transparent portion of the second layer becomes viewable through the transparent portion in response to the orientation changes associated with the predicted next pose (e.g., a new view of the mountainous landscape through the window shown in FIG. 6 is now viewable).

Some embodiments also determine when a previously overlapped portion of a first layer is still overlapped by a second layer even in response to the predicted next pose of the part of the computer system (e.g., the portion of the mountainous landscape near the bottom of the house in FIG. 6 is still overlapped). In response, these embodiments skip LSR processing of the overlapped portion of the first layer. To clarify, the embodiments apply LSR processing to some portions of the first layer while refraining from applying LSR processing to the overlapped portion of the first layer that is still overlapped by the second layer. As a result, the embodiments dynamically determine when LSR processing is avoidable and efficiently optimize the computer system's battery life by skipping LSR processing during those avoidable instances.

It will be appreciated that while most of this disclosure emphasizes generating pose data based on a pose of a HMD, this will not always be the case. For instance, the disclosed embodiments are also able to generate relational pose data between a HMD and a different on-body device (e.g., a handheld device, foot device, chest device, etc.) or even a device that is not positioned on a user's body (e.g., a base station that is positioned in a room and that is used to further enhance the mixed-reality experience by mapping and detailing the room's contents). Therefore, in addition to generating a scene based on the pose of the HMD, the embodiments are also able to generate the scene based on a relationship between the HMD and the various on-body and/or base devices. Here, a brief example will be helpful. Suppose the user is wearing a HMD and is holding a handheld device. When immersed in a scene, a laser gun may be visualized as being attached to the user's arm. To calculate the correct orientation and pose of the laser gun, the computer system relies on pose data collected from both the HMD and the handheld device. Accordingly, the embodiments discussed herein are not limited to generating a scene based solely on pose data acquired from a HMD. Rather, the embodiments are also able to generate a scene based on pose data collected from other types of on-body and/or base devices.

Accordingly, this disclosure presented systems, hardware storage devices, and methods that optimize LSR processing for computer-generated scenes that include multiple layers. Some embodiments cause the LSR processing to be selectively applied to various sub-regions of the layer. Other embodiments cause the LSR processing to be selectively applied to multi-layered scenes. As a result of these processes, the embodiments presented herein optimize and selectively apply LSR processing and can, thereby, help conserve power that would otherwise be expended by universal LSR processing.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system comprising:
one or more processor(s); and
one or more computer-readable hardware storage media having stored thereon computer-executable instructions that are executable by the one or more processor(s) to cause the computer system to optimize late stage reprojection by causing the computer system to:
generate, utilizing at least one graphical processing unit (GPU) located at the computer system, a rendered scene that includes a plurality of layers, including a first layer and a second layer;
in response to detecting a movement of the computer system, where the movement resulted in a movement threshold for the first layer being satisfied, trigger and apply late stage reprojection processing to the first layer, wherein the late stage reprojection processing of the first layer is completed at either the GPU or at a processor located at a display connected to the computer system;
apply late stage reprojection processing to the second layer, the late stage reprojection processing of second layer being performed independently from late stage reprojection processing of other layers of the plurality of layers, the late stage reprojection processing applied to the second layer including one or more transformation(s) that are applied to the second layer but that are not applied to the first layer, wherein the late stage reprojection processing of the second layer is applied utilizing the processor located at the display such that the late stage reprojection processing of the second layer is completed after the rendered scene is rendered by the at least one GPU but prior to being displayed at the display connected to the computer system;
create, at the processor located at the display, a unified layer by compositing the transformed second layer with the first layer; and
display the unified layer.

2. The computer system of claim 1, wherein the one or more transformation(s) include applying an invertible image transformation.

3. The computer system of claim 1, wherein execution of the computer-executable instructions further causes the computer system to pre-filter at least some pixels of the first layer by applying a pixel mask.

4. The computer system of claim 1, wherein execution of the computer-executable instructions further causes the computer system to pre-filter at least some pixels of the first layer by applying a vector mask.

5. The computer system of claim 4, wherein the at least some pixels of the first layer are identified as being edge pixels and are determined to contribute less to scene quality than non-filtered pixels.

6. The computer system of claim 1, wherein the one or more transformation(s) include applying a matrix transformation to at least some pixels included within the first layer.

7. The computer system of claim 1, wherein the scene is one of:
(i) mixed-reality scene, (ii) an augmented-reality scene, or (iii) a virtual-reality scene.

8. The computer system of claim 1, wherein a second movement threshold is associated with the second layer, and wherein the movement of the computer system satisfies the movement threshold for the first layer but does not satisfy the second movement threshold for the second layer.

9. The computer system of claim 1, wherein the scene is generated in response to multiple predicted poses of the computer system being generated, each predicted pose being associated with a corresponding probability of realization that is based, at least in part, on an event that is to subsequently occur, but that is not currently occurring, in the scene.

10. The computer system of claim 1, wherein the scene is generated in response to a first predicted pose of a part of the computer system, the first predicted pose being different than a previously acquired actual determined pose of the part of the computer system, and wherein, in response to the first predicted pose, the late stage reprojection processing of the first layer is applied to all pixels of the first layer and the late stage reprojection processing of the second layer is applied to all pixels of the second layer.

11. The computer system of claim 1, wherein the one or more transformations that are performed on the second layer include one or more of 1) a translation, 2) a reflection, 3) a rotation, or 4) a dilation.

12. The computer system of claim 1, wherein compositing the second layer with the first layer further includes generating a buffer region around the second layer.

13. One or more hardware storage device(s) having stored thereon computer-executable instructions that are executable by one or more processor(s) of a computer system to cause the computer system to optimize late stage reprojection by causing the computer system to:
   generate, utilizing at least one graphical processing unit (GPU) located at the computer system, a rendered scene that includes a plurality of layers, including a first layer and a second layer;
   in response to detecting a movement of the computer system, where the movement resulted in a movement threshold for the first layer being satisfied, trigger and apply late stage reprojection processing to the first layer, wherein the late stage reprojection processing of the first layer is completed at either the GPU or at a processor located at a display connected to the computer system;
   apply late stage reprojection processing to the second layer, the late stage reprojection processing of the second layer being performed independently from late stage reprojection processing of other layers of the plurality of layers, the late stage projection processing applied to the second layer including one or more transformation(s) that are applied to the second layer but that are not applied to the first layer, wherein the late stage reprojection processing of the second layer is applied utilizing the processor located at the display such that the late stage reprojection processing of the second layer is completed after the rendered scene is rendered by the at least one GPU but prior to being displayed at the display connected to the computer system;
   create, at the processor located at the display, a unified layer by compositing the transformed second layer with the first layer; and
   display, the unified layer.

14. The one or more hardware storage device(s) of claim 13, wherein compositing the transformed second layer with the first layer includes causing the transformed second layer to overlap a portion of the first layer, whereby the transformed second layer at least partially obfuscates the portion of the first layer.

15. The one or more hardware storage device(s) of claim 14, wherein the transformed second layer includes a transparent portion, and wherein, after the transformed second layer is caused to overlap the portion of the first layer, at least some of the overlapped portion of the first layer is visible through the transparent portion of the second layer.

16. The one or more hardware storage device(s) of claim 13, wherein the scene is determined based on information previously acquired by one or more hardware components of the computer system, the one or more hardware components including an accelerometer, a gyroscope, a magnetometer, a depth sensor, a camera, or an infrared sensor.

17. The one or more hardware storage device(s) of claim 13, wherein the late stage reprojection processing of the first layer is applied only to an identified subset of pixels that are included within the first layer.

18. The one or more hardware storage device(s) of claim 13, wherein the computer system renders the unified layer using foveated rendering.

19. The one or more hardware storage device(s) of claim 13, wherein compositing the transformed second layer with the first layer includes causing the transformed second layer to overlap a portion of the first layer, and wherein execution of the computer-executable instructions further causes the computer system to:
   generate a predicted next pose of the computer system;
   determine that at least a part of the overlapped portion of the first layer is still overlapped by the second layer even in response to the predicted next pose of the computer system; and
   apply late stage reprojection processing to a portion of the first layer while refraining from applying late stage reprojection processing to the at least the part of the overlapped portion of the first layer that is still overlapped by the second layer, whereby the computer system dynamically determines when late stage reprojection processing is avoidable.

20. The one or more hardware storage device(s) of claim 13, wherein rendering the unified layer is performed by rendering the unified layer on a head mounted display.

21. The one or more hardware storage device(s) of claim 13, wherein a difference between the late stage reprojection processing of the first layer and the late stage reprojection processing of the second layer is due to a variance in determined depth between the first layer and the second layer.

22. A method for optimizing late stage reprojection, the method being performed by one or more processor(s) of a computer system and comprising:
   generating, utilizing at least one graphical processing unit (GPU), a rendered scene that includes a plurality of layers, including a first layer and a second layer;
   in response to detecting a movement of the computer system, where the movement resulted in a movement threshold for the first layer being satisfied, triggering and applying late stage reprojection processing to the first layer, wherein the late stage reprojection processing of the first layer is completed at the GPU;
   applying late stage reprojection processing to the second layer, the late stage reprojection processing of the second layer being performed independently from late stage reprojection processing of other layers of the plurality of layers, the late stage projection processing applied to the second layer including one or more transformation(s) that are applied to the second layer but that are not applied to the first layer, wherein the late stage reprojection processing of the second layer is applied utilizing a processor located within a display connected to the computer system such that the late stage reprojection processing of the second layer is completed after the rendered scene is rendered by the at least one GPU but prior to being displayed at the display connected to the computer system;

creating, at the processor located within the display, a unified layer by compositing the transformed second layer with the first layer; and displaying the unified layer.

23. The method of claim 22, wherein the late stage reprojection processing of the second layer is applied to all pixels in the second layer while the late stage reprojection processing of the first layer is applied to only a subset of pixels in the first layer.

24. The method of claim 22, wherein the second layer includes a transparent portion such that, after the unified layer is rendered, a portion of the first layer is viewable through the transparent portion of the second layer.

25. The method of claim 22, wherein the method further includes:

generating a predicted next pose of the computer system; and creating a new unified layer by compositing the second layer with the first layer, wherein the portion of the first layer that was previously viewable through the transparent portion of the second layer is now obscured in response to orientation changes associated with the predicted next pose, and wherein a new portion of the first layer that was not originally viewable through the transparent portion of the second layer is now viewable through the transparent portion in response to the orientation changes associated with the predicted next pose.

* * * * *